(12) United States Patent
Ive et al.

(10) Patent No.: US 10,166,179 B2
(45) Date of Patent: Jan. 1, 2019

(54) FIXATIVE POLYMERS AND HAIR STYLING COMPOSITIONS THEREOF

(71) Applicant: ISP INVESTMENTS INC., Wilmington, DE (US)

(72) Inventors: Sharona Kelly Ive, West Yorkshire (GB); David Petty, Bradford (GB); Raymond Rigoletto, Jr., Denville, NJ (US); Maria Regina Bartuccio Raponi, São Paulo (BR)

(73) Assignee: ISP INVESTMENTS LLC, Wilmington, DE (US)

( * ) Notice: Subject to any disclaimer, the term of this patent is extended or adjusted under 35 U.S.C. 154(b) by 0 days.

(21) Appl. No.: 15/106,304

(22) PCT Filed: Dec. 22, 2014

(86) PCT No.: PCT/US2014/071910
§ 371 (c)(1),
(2) Date: Jun. 19, 2016

(87) PCT Pub. No.: WO2015/095870
PCT Pub. Date: Jun. 25, 2015

(65) Prior Publication Data
US 2016/0331666 A1    Nov. 17, 2016

Related U.S. Application Data

(60) Provisional application No. 61/918,832, filed on Dec. 20, 2013.

(51) Int. Cl.
*A61K 8/81* (2006.01)
*A61K 8/04* (2006.01)
(Continued)

(52) U.S. Cl.
CPC ............ *A61K 8/8152* (2013.01); *A61K 8/042* (2013.01); *A61K 8/8176* (2013.01);
(Continued)

(58) Field of Classification Search
CPC .... A61Q 5/06; A61K 8/8152; A61K 2800/48; A61K 2800/548; C08F 2220/1808; C08F 220/06
See application file for complete search history.

(56) References Cited

U.S. PATENT DOCUMENTS

2003/0207988 A1    11/2003    Tamareselvy et al.
2008/0219934 A1    9/2008    Kim et al.
(Continued)

OTHER PUBLICATIONS

International Search Report, PCT/US2014/71910 published on Jun. 25, 2015.

*Primary Examiner* — Jianfeng Song
(74) *Attorney, Agent, or Firm* — William J. Davis; Nathalie Tietcheu

(57) ABSTRACT

The present invention provides a fixative polymer derived from about 55-60% by weight of ethyl acrylate; about 30-50% by weight of (meth) acrylic acid; about 1-5% by weight of an associative monomer comprising a methacrylic ester with an oxyalkylated ethylenic unsaturation terminated by a hydrophobic, non-aromatic branched chain with 12 to 22 carbon atoms; and about 0.01-4% by weight of a cross-linking agent, personal care compositions comprising these fixative polymers and the use of these polymers in hair styling products.

7 Claims, 13 Drawing Sheets

(51) Int. Cl.
*C08F 220/18* (2006.01)
*A61Q 5/12* (2006.01)
*A61Q 5/06* (2006.01)

(52) U.S. Cl.
CPC .............. *A61K 8/8182* (2013.01); *A61Q 5/06* (2013.01); *A61Q 5/12* (2013.01); *C08F 220/18* (2013.01); *A61K 2800/30* (2013.01); *A61K 2800/48* (2013.01); *A61K 2800/548* (2013.01); *A61K 2800/594* (2013.01); *C08F 2220/1808* (2013.01)

(56) References Cited

U.S. PATENT DOCUMENTS

2010/0135918 A1 6/2010 Kim et al.
2013/0164242 A1 6/2013 Tamereselvy et al.

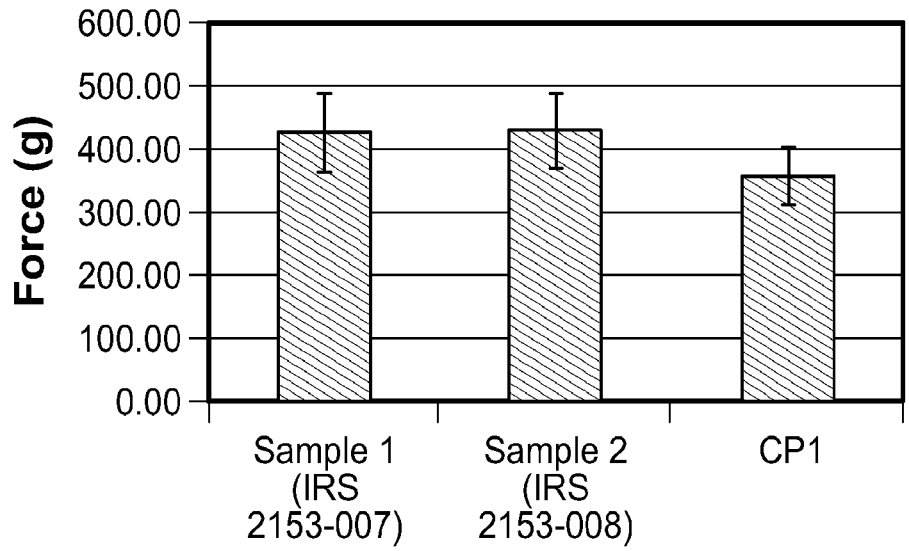
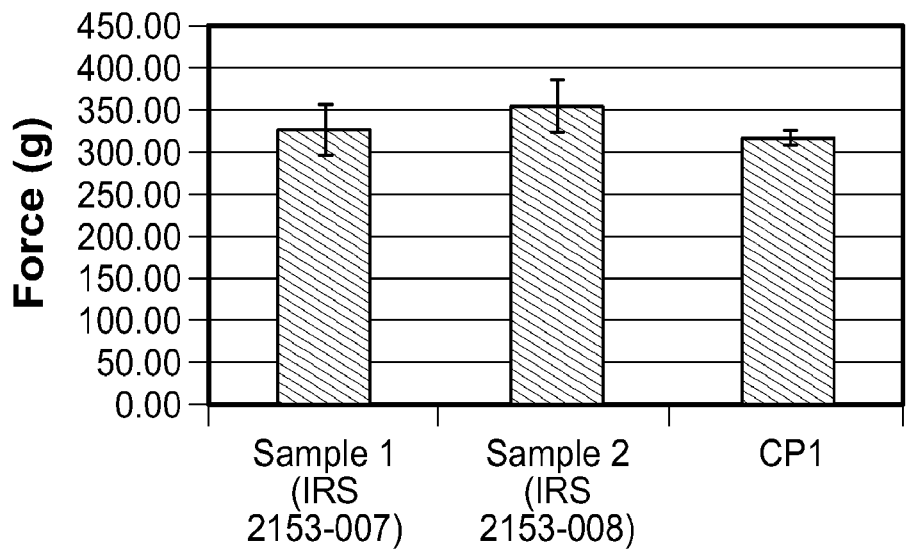
FIG. 1

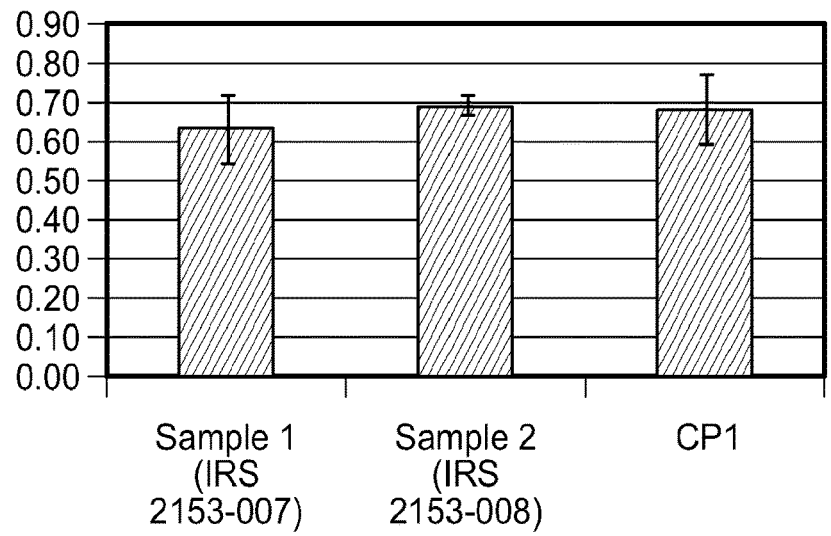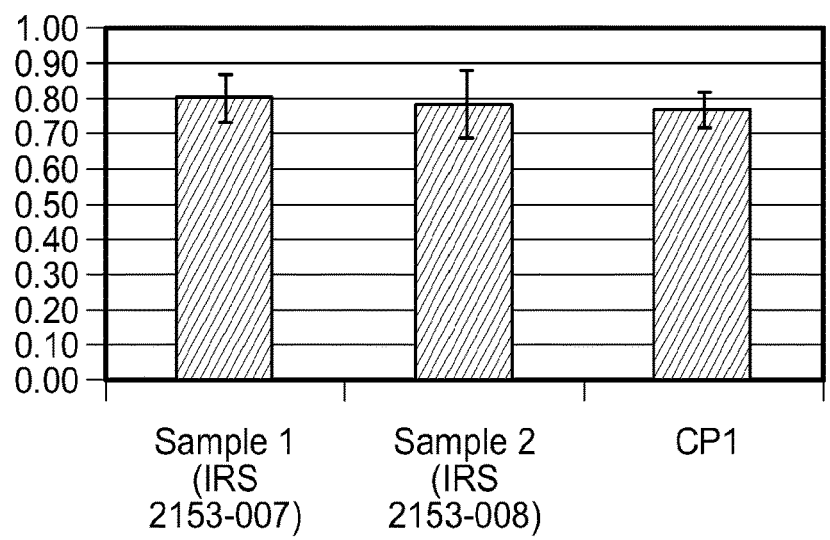
FIG. 2

FIXATIVE POLYMERS AND HAIR STYLING COMPOSITIONS THEREOF

FIELD OF THE INVENTION

The invention relates to fixative polymers, compositions comprising such fixative polymers and their applications in personal care compositions, and more specifically, to crystal clear hair styling gel compositions.

BACKGROUND OF THE INVENTION

EP13836 (assignee: Rohm & Haas) discloses emulsion polymers, which comprise (i) 20-69.5% by weight of (meth) acrylic acid, (ii) 0.5 to 25% by weight of a monomer of the formula $CH_2=C(R)-C-(O)-O-(CH_2CH_2O)N-R^0$, in which R is H of $CH_3$, n is at least 2 and $R^0$ is $C_8$-$C_{30}$-alkyl, and (iii) at least 30% by weight of a $C_1$-$C_4$-alkyl(meth) acrylate. This patent covers various hydrophobic monomer combinations with various acrylates in a plurality of weight ratios. However, there is no suggestion of the cross-linked polymer of the present invention, its combination of desirable properties or its use in personal care compositions.

U.S. Pat. No. 7,205,271 (assignee: ISP Investments Inc.) discloses a rheology modifier/hair styling resin which is a cross-linked, linear poly(vinyl amide/polymerizable carboxylic acid) copolymer exhibiting advantageous hair care properties. The resin exhibits high viscosity and long lasting curl retention.

U.S. Pat. No. 7,217,752 (assignee: Noveon Inc.) discloses an aqueous surfactant composition having cross-linked alkali-swellable acrylate copolymer as rheology modifier and an insoluble silicone compound. The copolymer is derived from ethyl acrylate, methacrylic acid, cross-linking agent and a hydrophobe.

U.S. Pat. No. 7,288,616 (assignee: Lubrizol Advanced Materials Inc.) discloses multipurpose alkali soluble associative polymers which are polymerization products of methacrylic acid; ethyl acrylate; first and second associative monomers along with a crosslinking agent and a chain transfer agent.

While different rheology modifiers, including associative alkali-soluble thickeners, have been disclosed in various applications, there still is the desire to find a composition which provides suitable thickening as well as the combination of stringent rheological and other properties desired for personal care applications.

Polymers for personal care compositions must not only perform the functional aspects of thickening, suspension and stabilization, but must also provide enhanced appearance to the finished product, superior flow and pour properties, crystal clarity, high humidity curl retention (HHCR), a smooth, light, cushiony feel in use, non-sticky (no tack) after drying, and a pleasant after-feel.

Despite the polymers proposed by the aforementioned patents and other approaches described in the published literature, there still exists a need for improved fixative polymers to achieve the desired rheological and aesthetic properties.

Thus, better styling polymers are desired which impart improved rheological, aesthetic and thickening properties to end use personal care products containing these polymers.

The inventive fixative polymers and their applications in personal care, particularly in clear hair styling gels, provide a combination of highly desired rheology properties without compromising on other aesthetic properties.

SUMMARY OF THE INVENTION

We have discovered a new, improved and effective fixative polymer for providing a unique combination of properties, including desirable rheology effects. The invention provides compositions and methods for delivering improved viscosity and rheology benefits in personal care compositions.

In accordance with the present invention, there is provided a fixative polymer derived from:
a) about 55-60% by weight of ethyl acrylate;
b) about 30-50% by weight of (meth) acrylic acid;
c) about 1-5% by weight of an associative monomer comprising a methacrylic ester with an oxyalkylated ethylenic unsaturation terminated by a hydrophobic, non-aromatic branched chain with 12 to 22 carbon atoms; and
d) about 0.01-4% by weight of a cross-linking agent.

Monomer a) is ethyl acrylate present in an amount of about 55-60%, preferably 56-58% by weight of the total polymer. Monomer b) is methacrylic acid present in amount of about 30-50% preferably 30-40% by weight of the total polymer. Monomer c) is a (meth)acrylic ester of an ethoxylated (25 mol EO) $C_{16}$-$C_{18}$ fatty alcohol present in an amount of about 1-5% by weight of the total polymer. A preferred cross-linking agent is pentaerythritol triallyl ether (PETE) present in an amount of about 0.01 to 4%, preferably 0.01 to 1% and more preferably 0.01 to 0.05% by weight of the total polymer.

The present invention provides personal care compositions comprising:
i) the above-described fixative polymer;
ii) personal care additives including auxiliary fixative polymers; and
iii) an aqueous carrier.

The present invention provides applications of fixative polymers in personal care and topical health care comprising any cosmetic, toiletry, and topical pharmaceutical formulation that require rheology modification or thickening selected from shampoos, chemical and non-chemical hair curling and hair straightening products, hair style maintenance products, emulsion lotions and creams for the nails, hands, feet, face, scalp, and body, hair dyes, face and body makeup, nail care products, astringents, deodorants, antiperspirants, depilatories, skin-protective creams and lotions, such as sunscreens, skin and body cleansers, skin conditioners, skin toners, skin firming compositions, shampoos, liquid soaps, soap bars, bath products, and shaving products. A preferred application is a fixative gel.

The present invention provides personal care compositions, containing the above-described fixative polymer in water, in its neutralized or anionic form at a pH in the range of about 3 to about 9. The polymers provide compositions featuring a Brookfield viscosity ranging from about 100 mPas to 100,000 mPas or more (Brookfield RVT, 20 rpm, at about 25° C.-ambient room temperature).

Desirably, the present fixative polymers are compatible with either traditional Carbomer polymers or with hydrophobically-modified Carbomer polymers. Carbomers are homopolymers of acrylic acid which is crosslinked or bonded with any of several poly alcohol and/or alkyl ethers. Carbomers are used widely commercially as thickeners and emulsion stabilizers in cosmetic products. The viscosity produced by such combinations was unexpectedly higher than the sum of the viscosities of currently available commercial gels with comparable concentrations.

The present invention provides polymeric compositions which are soluble in the hair styling composition "as is" or upon neutralization of some or all of the acid groups contained in the polymer composition. The acidic groups in the polymer mixture of this invention, such as carboxylic acid groups, may be neutralized by conventional techniques with at least one base to dissolve the polymer in the hair styling composition.

The inventive fixative polymeric compositions are used in providing hair setting compositions which include hair styling, hair fixative, and hair grooming products that are conventionally applied to the hair (wet or dry) in the form of gels, rinses, emulsions, (oil-in-water, water-in-oil or multiphase), such as lotions and creams, pomades, sprays (pressurized or non-pressurized), spritzes, foams, such as mousses, shampoos, solids such as sticks, semi-solids and the like, or are applied from a hair setting aid having the hair setting composition impregnated therein or coated thereon, to leave the hair setting agent in contact on the hair for some period until removed as by washing.

The present invention further provides hair styling compositions comprising styling polymer in an amount of about 0.01 wt % to about 20 wt %, preferably, from about 0.05 wt % to about 15 wt %, from about 0.1 wt % to about 10 wt %, from about 0.1 wt % to about 5 wt %, from about 0.1 wt % to about 1 wt %, or from about 0.5 wt % to about 1 wt % of total hair styling composition.

The present invention provides crystal clear (% Transmittance more than 90) hair styling compositions with at-least 90% high humidity curl retention, and stiffness durability of at-least 0.7.

DESCRIPTION OF THE DRAWINGS

An exemplary embodiment of the present invention is illustrated by way of example in the accompanying drawings in which like reference numbers indicate the same or similar elements and in which:

FIG. 1 is a graphical presentation of Stiffness by Texture Analysis;

FIG. 2 is a graphical presentation of Stiffness Durability;

DETAILED DESCRIPTION OF THE INVENTION

Figure 3:
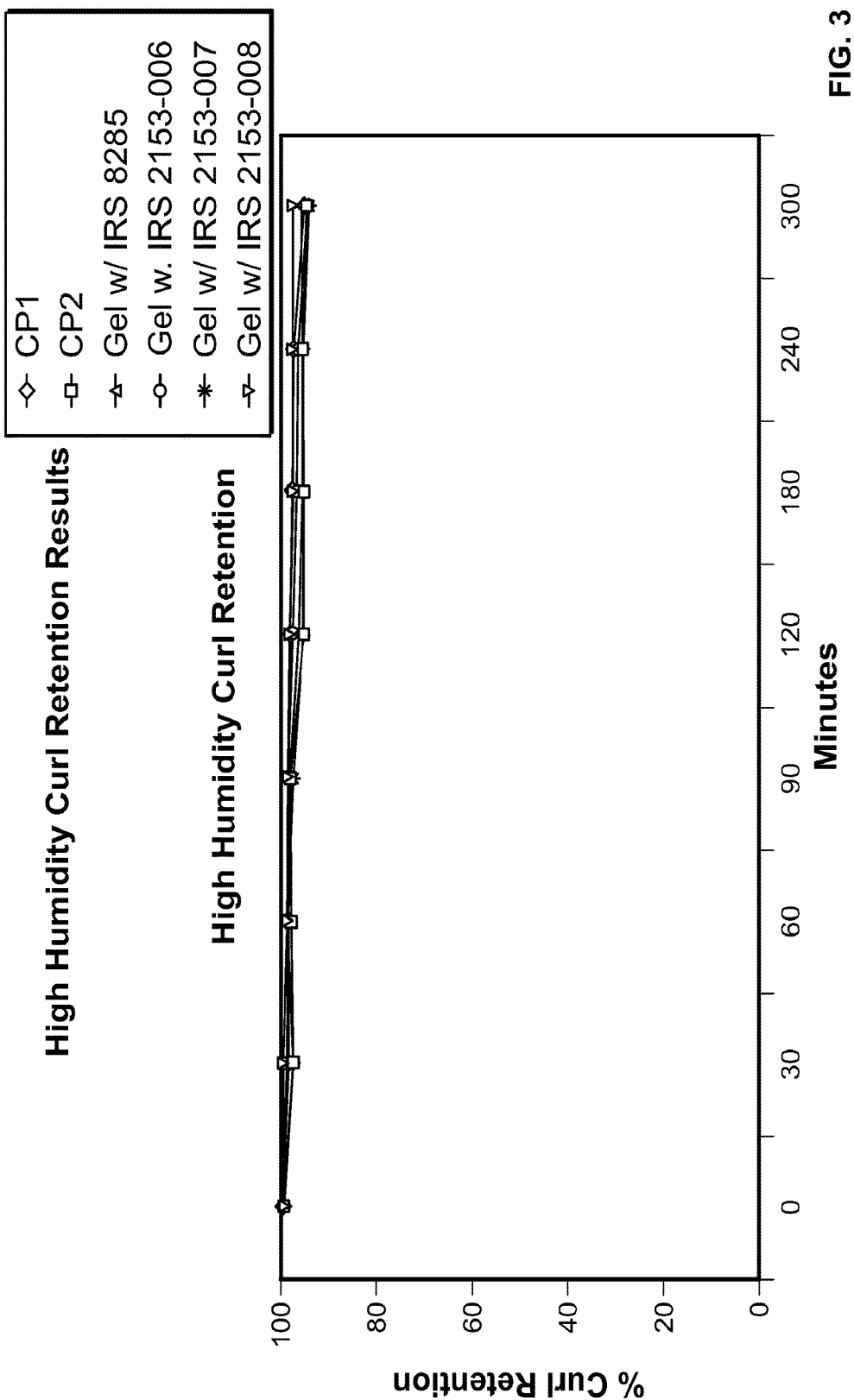
FIG. 3 is a graphical presentation of High Humidity Curl Retention Results.

While applicants do not wish to be bound by any theories, it is believed that the inventive compositions provide more effective polymers acting as rheology modifiers than those in the existing literature, and in this way provide improved and more effective personal care compositions.

Today's fixative polymers must offer not only the functional aspects of thickening, suspension and stabilization, but must also provide enhanced appearance to the finished product; superior flow and pour properties; crystal clarity, a smooth, light, cushiony feel in use, non-sticky after drying, and a pleasant after-feel.

The term 'aesthetic property' refers to visual and tactile psycho-sensory product properties such as color, clarity, smoothness, tackiness, lubricity, texture, and the like.

The term 'appropriate amount' refers to quantity of monomer sufficient enough to perform the desired function.

The term 'clarity' refers to measurement of turbidity levels when a polymer is dissolved in a solution. The test is conducted by passing a beam of light through a hair gel formulation and measuring the percentage of light loss. A sample measuring % T more than 90 when light is passed through a solution containing the sample is considered to be crystal clear.

The term 'curl retention' refers to polymer ability to hold a set after absorption of water from the applied formula or from the surrounding atmosphere. This characteristic is tested by the use of the high humidity curl retention (HHCR) technique, which measures the percent curl retention as a function of time to a humid atmosphere.

The term 'fixative' refers to polymer having properties of film-formation, adhesion, or coating deposited on a surface on which the polymer is applied.

The term 'flexibility' refers to property of an object such as hair, which describes that the object is capable of being flexed, turned, bowed or twisted without breaking.

The term 'hair styling and hair fixative' refer collectively to hair setting agents that are hair fixatives and film formers and which are topically applied to the hair to actively contribute to the ease of styling and/or holding of a hair set, and to maintain the restylability of the hair set.

The term 'polymerization initiator' refers to chemical species that reacts with monomer to form an intermediate compound capable of linking successively with a large number of other monomers into a polymeric compound.

The term 'rheology' refers to properties like Brookfield Viscosity, increase or decrease in viscosity in response to shear stress, flow characteristics, gel properties such as stiffness, resilience, flow ability, foam properties such as foam stability, foam density, ability to hold a peak and the like, and aerosol properties such as ability to form aerosol droplets when dispensed from propellant based or mechanical pump-type aerosol dispensers.

The term 'resilience' refers to mechanical property of material such as hair, which implies free return to a previous position, shape or condition after deformation.

The term 'surfactant' refers to chemical compound which, when dissolved in water, concentrate at surfaces (interfaces) such as water-air or water-oil depending on their molecular structure giving rise to wide range of surface chemistry functions such as wetting, emulsifying, solubilising, foaming/defoaming, rheology-modifying, antistatic, glossing, lubricity and surface conditioning.

The term 'stiffness' refers to the amount of force it takes to deform a polymer film or more specifically, a hair bundle treated with a polymer. Stiffness is one of the important mechanical properties of a hair fixative.

The term 'texture analyzer' refers to an instrument to measure mechanical properties like stiffness, flexibility of an object such as hair.

In one embodiment, the present invention provides rheology modifying fixative polymers derived from monomers: ethyl acrylate; (meth) acrylic acid; associative monomer; and cross-linking agent.

In another embodiment, the present invention provides personal care compositions containing such fixative polymers, particularly in fixative hair care compositions.

Fixative polymers of the present invention ideally should contain the following properties desired for hair care compositions:

Gel containing the polymer should be crystal clear
Gel containing the polymer should be easily scooped from a jar
Must have good pick-up
Should spread all-through the surface
Must possess pseudo plasticity and desired rheological properties.
Should have more mechanical stiffness, durability and other advanced styling benefits; and
Should possess improved High Humidity Curl Retention (HHCR) with no lag After numerous experimental trials, the present inventors observed that each monomer of the above-described polymer has to be present in specific appropriate amounts to achieve the combinations of desired effects.

The monomer methacrylic acid, if present in excess to the appropriate amount makes the product more acidic, which in-turn requires more amounts of base to neutralize during formulation stage.

The hydrophobe containing associative monomer, if present in excess to the appropriate amount, does not achieve the desired rheology. If present in lesser than the appropriate amount, the curl retention in hair decreases. Compatibility of the polymer as film forming agent or its performance on the hair can be affected.

The cross-linking agent if present in excess to the appropriate amount renders the structure unstable and it may collapse. If the cross-linking agent is present in less than the appropriate amount or completely absent, the resulting product is choppy (non-smooth) and cannot be easily scooped from a jar containing the product.

It was surprisingly observed that the increase in one monomer to achieve one property will generally hinder all other desired properties. For instance, if hydrophobic chain length in an associative monomer is increased to increase the rheology and viscosity of the polymer, then clarity of the polymeric product gets adversely affected. The combination of monomeric components in the polymer in the selected amounts results in achieving all the desired performance benefits.

Hence a product with a combination of all properties is achieved by incorporating the appropriate amount of each monomer into making the fixative polymer.

Fixative polymers of the present invention are derived from:
about 55-60% by weight of ethyl acrylate;
about 30-50% by weight of (meth) acrylic acid;
about 1-5% by weight of an associative monomer comprising a methacrylic ester with an oxyalkylated ethylenic unsaturation terminated by a hydrophobic, non-aromatic branched chain with 12 to 22 carbon atoms; and
about 0.01-4% by weight of a cross-linking agent.

The ethyl acrylate is present in an amount of about 55-60%, preferably 56-58% by weight of the total polymer.

The methacrylic acid is present in an amount of about 30-50% preferably 30-40% by weight of the total polymer.

The associative monomer c) is a methacrylic ester with oxyalkylated ethylenic unsaturation terminated by a hydrophobic, non-aromatic branched chain with 12 to 22 carbon atoms. Particularly associative monomer is (meth)acrylic acid ester of a mixture of ethoxylated $C_8$-$C_{30}$ alkyl chain, preferably $C_{12}$-$C_{30}$, in particular $C_{16}$-$C_{22}$ fatty alcohols, wherein the ethoxylated alcohols in each case comprise 20 to 30 ethylene oxide (EO) radicals (commonly referred to as "$C_{16-18}$ alkyl-PEG1100 methacrylates"). Such $C_{16-18}$alkyl-PEG1100 methacrylates are commercially available for example as Plex® 877-0 (25% strength by weight preparation in methyl methacrylate) or Lutencryl® 250 (50% strength by weight solution in methacrylic acid) or VISIOMER® C18 PEG 1105 MA. Preferred associative monomer is methacrylic ester of an ethoxylated (25 moles EO) $C_{16}$-$C_{18}$ fatty alcohol (VISIOMER® C18 PEG 1105 MA) having the structural formula:

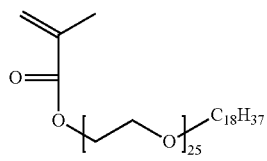

Visiomer PEG C18 1105 MA

The associative monomer is present in an amount of about 1-5%, preferably 2-4% by weight of the total polymer.

The cross-linking agent can be selected from conventional cross-linking agents such as divinyl ethers of an aliphatic diol of 1,2-ethanediol, 1,3-propanediol, 1,4-butanediol, 1,5-pentanediol, 1,6-hexanediol, 1,7-heptanediol, 1,8-octanediol, 1,9-nonanediol, 1,10-decanediol, 1,11-undecanediol, and 1,12-dodecanediol, or divinyl ethers of diethylene glycol of triethylene glycol, tetraethylene glycol, pentaethylene glycol; hexaethylene glycol, heptaethylene glycol, octaethylene glycol, nonaethylene glycol, decaethylene glycol; or polyalkylene glycols and acrylates thereof of polyethylene glycol diacrylate, trimethylolpropane triacrylate, propylene glycol diacrylate, polyhydric alcohols esterified once or twice with acrylic acid triallylamine, tetraallylethylenediamine, diallyl phthalate, pentaerythritol triallyl ether, pentaerythritol triacrylate, pentaerythritol tetra-acrylate, N,N'-divinylimidazolidone, triallyl-1,3,5-triazine-2,4,6(1H,3H,5H)-trione and 2,4,6-triallyloxy-1,3,5-triazine. The preferred cross-linking agent is pentaerythritol triallyl ether (PETE) and in an amount of about 0.01 to 5%, preferably 0.01 to 1% and more preferably 0.01 to 0.05% by weight of the total polymer.

The fixative polymers of this invention can be manufactured by conventional polymerization techniques such as emulsion polymerization by standard processes known in the literature. Typically the process includes carrying out polymerization at temperature in the range of about 30-95° C. Polymerization can be carried out in presence of anionic surfactants, such as fatty alcohol sulfates or alkyl sulfonates, nonionic surfactants, such as linear or branched alcohol ethoxylates, amphoteric surfactants, or mixtures thereof. The emulsion polymerization reaction mixtures also includes free radical initiators performed in an aqueous or aqueous alcohol medium at a low pH, i.e., preferably not more than about 4.5.

Suitable initiators can be selected from hydrogen peroxide, peracetic acid, t-butyl hydroperoxide, di-t-butyl peroxide, dibenzoyl peroxide, benzoyl hydroperoxide, 2,4-dichlorobenzoyl peroxide, 2,5-dimethyl-2,5-bis(hydroperoxy) hexane, perbenzoic acid, t-butyl peroxypivalate, t-butyl per acetate, dilauroyl peroxide, dicapryloyl peroxide, distearoyl peroxide, diisopropyl peroxydicarbonate, dodecyl peroxydicarbonate, dieicosyl peroxydicarbonate, di-t-butyl perbenzoate, azobisisobutyronitrile, 2,2'-azobis-2,4-dimethylvaleronitrile, ferrous ammonium sulfate, ammonium persulfate, potassium persulfate, sodium persulfate and sodium perphosphate.

In another embodiment, the present invention provides a personal care composition comprising:
the above-described fixative polymer;
optionally, at least one other fixative polymer to adjust performance properties on hair;
personal care additives; and
an aqueous carrier. The fixative polymers and personal care additives are known in the art.

One or more surfactants may be added to the personal care compositions, typically to reduce the surface tension of the composition. When surfactants are present in the hair styling composition, they are preferably present at a concentration of from 1 to 7%, based on the total weight of the composition.

Surfactants can be anionic, non-ionic, cationic or amphoteric in nature. Non-limiting examples of the surfactants which can be used, alone or as mixtures are selected from the group comprising alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, α-olefin sulphonates, paraffin sulphonates, alkyl sulphosuccinates, alkyl ether sulphosuccinates, alkylamide sulphosuccinates, alkyl sulphosuccinamates, alkyl sulphoacetates, alkyl ether phosphates, acyl sarcosinates, acyl isethionates and N-acyltaurates and their salts thereof, polyethoxylated fatty acids, polypropoxylated fatty acids and polyglycerolated fatty acids, alkylphenols, α-diols and alcohols, polyethoxylated fatty amides comprising, for example, from 2 to 30 mol of ethylene oxide, polyglycerolated fatty amides comprising from 1 to 5 glycerol groups, and, for example, from 1.5 to 4 glycerol groups; oxyethylenated fatty acid esters of sorbitan comprising from 2 to 30 mol of ethylene oxide; fatty acid esters of sucrose, fatty acid esters of polyethylene glycol, alkylpolyglycosides, N-alkylglucamine derivatives, amine oxides, such as ($C_{10}$-$C_{14}$)alkylamine oxides and N-acylaminopropylmorpholine oxides, aliphatic secondary and tertiary amine derivatives chains comprising from wherein the at least one aliphatic group is chosen from linear and branched 8 to 18 carbon atoms and comprising at least one water-soluble anionic group (for example, carboxylate, sulphonate, sulphate, phosphate and phosphonate); ($C_8$-$C_{20}$) alkylbetaines, sulphobetaines, ($C_8$-$C_{20}$)alkylamido($C_1$-$C_6$) alkyl betaines and ($C_8$-$C_{20}$) alkylamido ($C_1$-$C_6$)alkylsulphobetaines and preferably sodium lauryl sulfate.

Auxiliary Fixative Polymers and Film Formers.

In a preferred embodiment, the personal care composition of this invention comprises at least one auxiliary fixing agent in combination with the fixative polymer of this invention. Suitable auxiliary polymer fixing agents include PVP, VP/VA Copolymer, VP/DMAEMA Copolymer, Polyquaternium-69, and Octylacrylamide/Acrylates/Butylaminoethyl Methacrylate Copolymer. Other contemplated fixing agents and film formers are described in U.S. Pat. No. 7,205,271 B2.

Various other personal care additives and conventional adjuvants well known in the art can be used, including, without being limited thereto, acidifying or alkalizing pH adjusting agents and buffering agents; auxiliary fixatives and film formers that modify the on hair attributes of the polymer of the present invention, such as gums, resins, polymers of synthetic or natural origin, and the like; auxiliary rheology modifiers, such as viscosity-increasing polymeric thickeners or gellants, additives, such as emulsifiers, emulsion stabilizers, waxes, dispersants, and the like, and viscosity control agents, such as solvents, electrolytes, and the like; hair and skin conditioning agents, such as antistatic agents, synthetic oils, vegetable or animal oils, silicone oils, monomeric or polymeric quaternized ammonium salts, emollients, humectants, lubricants, sunscreen agents, and the like; chemical hair waving or straightening agents; hair colorants, such as pigments and dyes for temporary, semi-permanent, or permanent hair dyeing; surfactants, such as anionic, cationic, nonionic, amphoteric and zwitterionic surfactants; polymer film modifying agents, such as plasticizers, humectants, tackifiers, detackifiers, wetting agents and the like, product finishing agents, such as chelating agents, opacifiers, pearlescing agents, preservatives, fragrances, solubilizers, colorants, such as pigments and dyes, UV absorbers, and the like; propellants (water-miscible or water-immiscible), such as fluorinated hydrocarbons, liquid volatile hydrocarbons, compressed gases, and the like; and mixtures thereof. In a preferred embodiment, the personal care composition of this invention features the above described polymer in combination with a UV absorber in the form of a crystal clear hair gel.

In preferred embodiments, the personal care composition can comprise at least 85%, more preferably 90% by weight water.

In another embodiment, the present invention provides compositions having inventive fixative polymers for personal care and topical health care and can comprise any cosmetic, toiletry, and topical pharmaceutical formulation that require rheology modification or thickening known from the cosmetic and pharmaceutical literature. Typical personal care formulations that can include the fixative polymer as a rheology modifier comprise, without being limited thereto, shampoos, chemical and non-chemical hair curling and hair straightening products, hair style maintenance products, emulsion lotions and creams for the nails, hands, feet, face, scalp, and body, hair dyes, face and body makeup, nail care products, astringents, deodorants, antiperspirants, depilatories, skin-protective creams and lotions, such as sunscreens, skin and body cleansers, skin conditioners, skin toners, skin firming compositions, liquid soaps, soap bars, bath products, shaving products, and the like. Formulated compositions for topical health care that are applied to the skin and mucous membranes for cleansing or soothing are compounded with many of the same physiologically tolerable cosmetic ingredients and chemically inert ingredients employed for personal care products in the same product forms, differing primarily in the purity grade of ingredients and by the presence of topically active medicaments.

In another embodiment, the inventive fixative polymers minimize or eliminate the need for added thickeners. Nonetheless for commercial applications, the fixative polymers can be used in combination with conventional polymeric thickeners, such as natural gums, resins, polysaccharides, synthetic polymeric thickeners, and the like, popularly used in the art. These polymers surprisingly are quite compatible with either traditional Carbomers polymer or with hydrophobically-modified Carbomer polymers and the viscosity produced by such combinations were unexpectedly higher than the sum of the viscosities of currently available commercial gels with comparable concentrations. This beneficially allows the use of fixative polymer in formulations containing Carbomer polymers or hydrophobically modified Carbomer polymers, if desired, to further enhance the aesthetic and rheological properties of the formulation. Compatibility of the polymer with Carbopol polymers allows for creation of a wide variety of novel styling products.

In a preferred embodiment, the present inventive polymers are used in making hair styling compositions in the form of a crystal clear gel.

Accordingly, the polymeric compositions are soluble in the hair styling composition "as is" or upon neutralization of some or all of the acid groups contained in the polymer composition. The acidic groups in the polymer mixture of this invention, such as carboxylic acid groups, may be neutralized by conventional techniques with at least one base to dissolve the polymer in the hair styling composition.

Non-limiting examples of neutralizing agents include inorganic bases such as alkali hydroxides selected from sodium hydroxide, potassium hydroxide, and ammonium hydroxide; organic bases such as triethanolamine (TEA), L-arginine, aminomethyl propanol, tromethamine (2-amino 2-hydroxymethyl-1,3-propanediol), PEG-15 cocamine, diisopropanolamine, triisopropanolamine, or tetrahydroxypropyl ethylene diamine.

The present inventive fixative polymers, when neutralized with a base, become more soluble in water. The polymer opens and develops viscosity with high clarity at approximately pH 6.5. This result in ionic repulsion and three dimensional expansion of the microgel network thus resulting in an increase in viscosity and other rheological properties. Thus these polymers modify or improve rheology characteristics of gel textures and emulsions which are more flowable, shear thinning and make the products aesthetically acceptable for personal care use.

Accordingly, a concentration of about 1% by weight of total personal care composition of inventive fixative polymer in deionized water, in its neutralized or anionic form at a pH in the range of about 3 to about 9, can provide a Brookfield viscosity ranging from about 100 mPas to 100,000 mPas or more (Brookfield RVT, 20 rpm, at about 25° C.-ambient room temperature).

The minimum amount of neutralizer added to the hair styling composition is that amount needed to provide solubility of the polymer mixture in the hair styling composition and to ensure that the pH or the hair styling composition is cosmetically acceptable. Typically from 5 to 100%, preferably from 10 to 100%, more preferably from 50 to 100%, and most preferably from 75 to 100%, based on molar equivalents, of the acid groups in the hair fixative resins are neutralized.

In another preferred embodiment, the inventive polymeric compositions are used in providing hair setting compositions which include hair styling, hair fixative, and hair grooming products that are conventionally applied to the hair (wet or dry) in the form of gels, rinses, emulsions, (oil-in-water, water-in-oil or multiphase), such as lotions and creams, pomades, sprays (pressurized or non-pressurized), spritzes, foams, such as mousses, shampoos, solids such as sticks, semi-solids and the like, or are applied from a hair setting aid having the hair setting composition impregnated therein or coated thereon, to leave the hair setting agent in contact on the hair for some period until removed as by washing.

Known preservatives may be used in the personal care hair styling composition including, for example, one or more of isothiazolones, iodopropynylbutyl carbamate, benzyl alcohol, imidazolidinylurea, and alkyl parabens. The preservatives preferably comprise from 0.001 to 1% active ingredient, in the hair fixative resin emulsion.

In addition to the fixative polymeric compositions of this invention, personal care hair styling compositions may contain any other ingredient used in cosmetics such as, for example, perfumes, dyestuffs which can color the hair styling composition itself or hair fibers, preservatives, sequestering agents, thickeners, silicones, softeners, foam synergistic agents, foam stabilizers, sun filters, peptizing agents, conditioning agents, shine agents, proteins, herbals, botanicals, neutralizers, plasticizers, and anionic, non-ionic, cationic, or amphoteric surfactants, or mixtures thereof.

The fixative polymer is preferably present in the personal care composition in a hair-styling effective amount, e.g., in an amount effective to promote at least about 90% curl retention in the hair after about 5 hours under conditions of about 90% relative humidity and a temperature about 24° C., when the composition is applied to human hair.

The personal care composition can include the fixative polymer, e.g., in an amount of from about 0.01 wt % to about 20 wt %, from about 0.05 wt % to about 15 wt %, from about 0.1 wt % to about 10 wt %, from about 0.1 wt % to about 5 wt %, from about 0.1 wt % to about 1 wt %, or from about 0.5 wt % to about 1 wt % of total hair styling composition.

Texture Analyzer

In cosmetic applications, texture is an important attribute that is sensed by the hands, lips, skin, hair and scalp. It encompasses the product's feel, such as the hardness of a soap bar. It also encompasses that product's effectiveness, such as the ability of a conditioner to soften hair. Texture affects processing and handling, and influences buying habits and consumer acceptance of products. It is used to quantify the mechanical properties of polymer treated surface such as hair. Texture analyzer instrumental set-up is illustrated in the following reference: J. Jachowicz and K. Yao, Dynamic Hair Spray Analysis. I. Instrumentation and preliminary results, J. Soc. Cosmet. Chem., 47, 73-84 (March/April 1996), FIG. 1, pg. 76.

Hair Styling Characteristics

Stiffness

Stiffness is an aesthetic property of hair. Mechanical stiffness evaluation is a method used to characterize polymer stiffness on hair tresses. To characterize the stiffness of a fixative polymer, peak force (g) is measured using a TA.XT.Plus® Texture Analyzer with a three point bend fixture where the hair tress is rested on two supports. Tests were conducted on inventive polymer under controlled environmental conditions (50% and 90% relative humidity (RH)) are shown in Figure. Hair tresses were treated with test formulations and the peak force (g) was measured using the three-point bend test. The peak force was then compared between formulations to assess the formulation with the greatest stiffness.

In stiffness tests on hair tresses, inventive polymer samples were evaluated and compared to other commercially available polymers. Results have been shown graphically in FIG. 2. Sample 1 and Sample 2 (inventive polymers) showed increase in peak force (above 400 and 320) as compared to the commercial polymer CP1 which showed a peak force (below 400 and 320) at 50% RH and 90% RH respectively.

Stiffness Durability

Stiffness Durability is measured by stiffness and flexibility parameters $F_1$—maximum force in $1^{st}$ deformation
$F_{10}$—maximum force in the $10^{th}$ deformation
Stiffness Ratio—stiffness of hair treated with fixative composition divided by untreated hair
$F_{10}/F_1$—ratio of maximum forces in the $10^{th}$ and $1^{st}$ deformation-mechanical durability.

In stiffness durability tests on hair tresses, inventive polymer samples were evaluated and compared to other commercially available polymers. The results are graphically represented in FIG. 3. Sample 1 and 2 having the inventive polymers show stiffness durability of at-least 7.

High Humidity Curl Retention (HHCR)

The HHCR test measures the percent curl retention of hair tresses, in 90% relative humidity at 25° C., as a function of time. This is a test performed by wrapping hair tresses around rollers in an overlapping configuration, allowing them to dry, and then carefully removing the tresses from the roller. The dried curled tresses are hung in a humidity cabinet and evaluated for curl droop over time. The curl retention test is a measure of the relative strengths of the hair and the fixative polymer, which oppose one another as the hair tress is driven to return to its natural configuration. In a more stringent test, the hair tresses were carefully wrapped around spiral curling rods so as not to twist the hair. The curled tresses were carefully removed from the spiral curling rods and placed in a humidity chamber, controlled at 50% & 90% RH. Measurements were taken at regular time intervals to determine the effect of humidity on curl retention. The percent spiral curl retention was determined by the formula used for traditional HHCR test:

% curl retention=$(L-L_t)/(L-L_0)*100$; wherein

Figure 4:
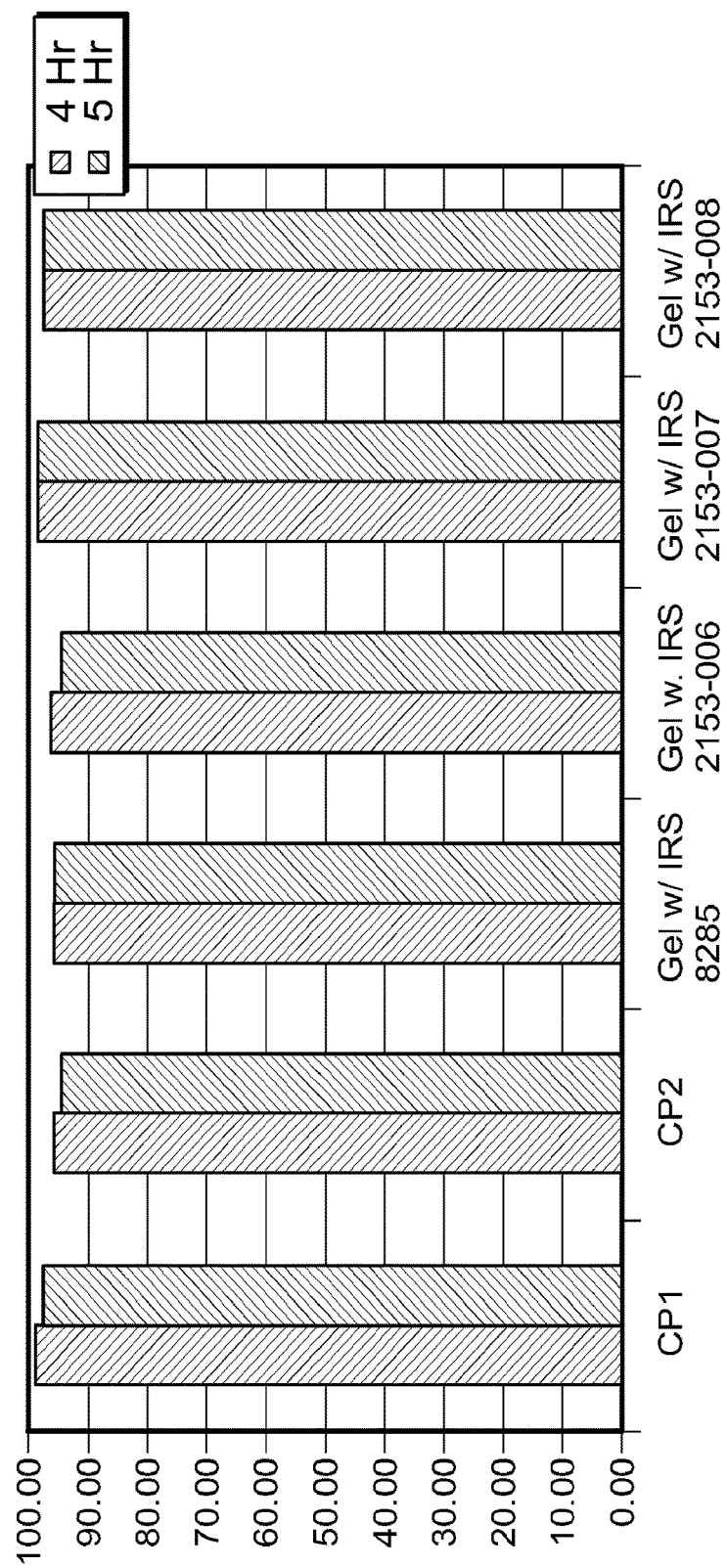
FIG. 4 is a graphical presentation of HHCR at 4 hr and 5 hr.
Figure 5:
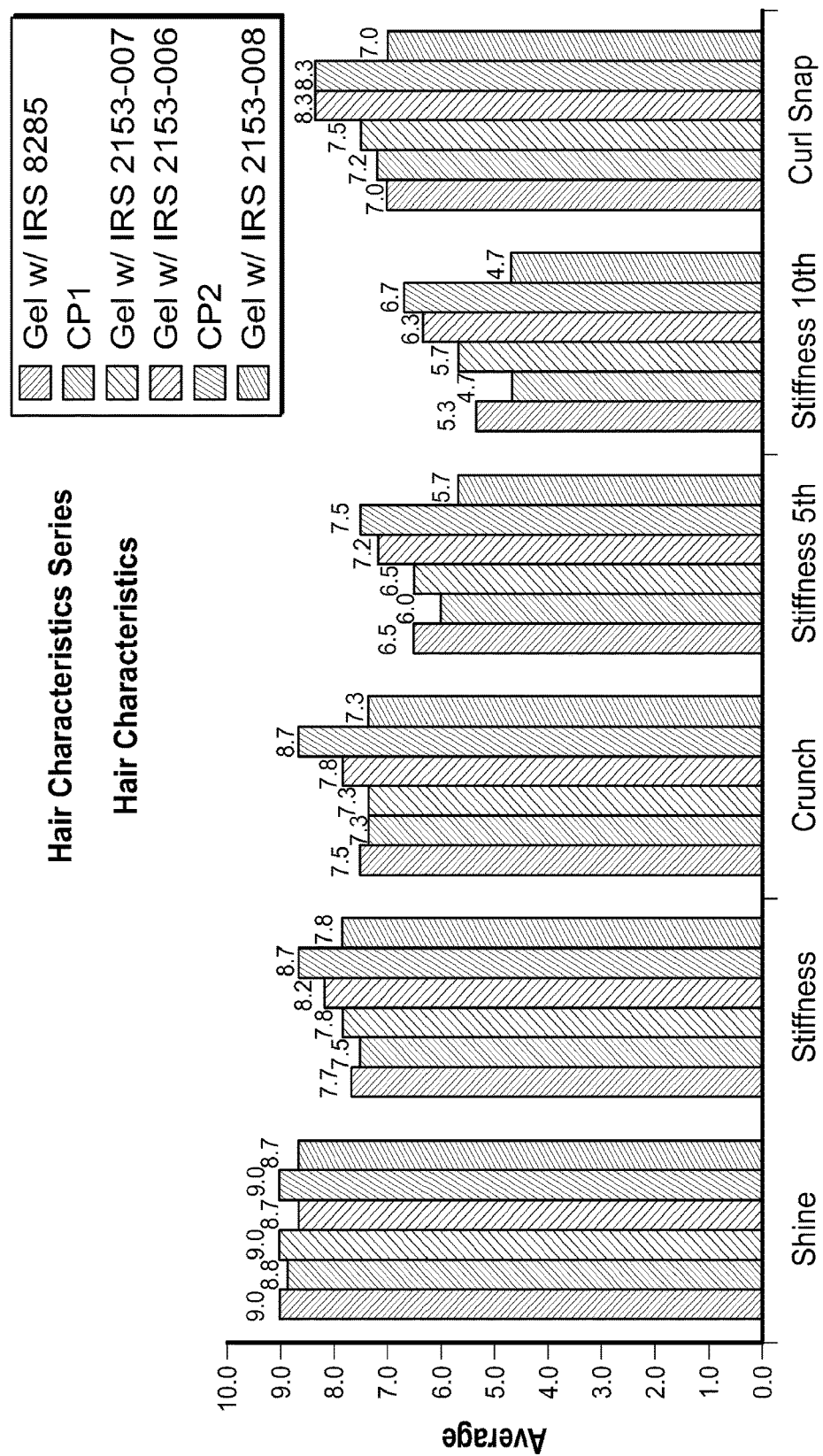
FIG. 5 is a comparison chart of Hair Characteristics series.

L is the total length of the hair tress,
$L_t$ is the length of the tress at the time interval observed and
$L_0$ is the initial length of the curled tress at the start of the test Simple hair fixative gels were prepared and were tested for HHCR. The results are graphically presented in FIGS. 4 and 5. It was observed that inventive fixative polymers showed 90% HHCR at-least for about 4 or 5 hours.

The inventive polymers are feasible to be customized to meet the ever challenging hair styles. The polymer provides excellent styling properties, stiffness, stiffness durability, non-sticky, retain curl even at high humid conditions. Inventive fixative polymers are formulated according to preference by altering the concentration and pH.

Clarity

Clarity is measurement of turbidity levels when a polymer is dissolved in a solution. The test is conducted by passing a beam of light through a hair gel formulation and measuring the percentage of light loss. Amount of light passed through the solution without getting refracted is measured as % T [transmittance]. Inventive fixative polymers give % T more than 90, thus making the polymeric gel crystal clear. Working Example 3 discloses composition comprising various levels of styling polymer with Carbomer. % Transmittance of light having wavelength of 455 nm was allowed to pass through the samples of Formula 5A, 5B, 5C, 6A, 6B & 7B. Values of % T of 90 and above were reported for the above samples. This indicates the samples containing fixative polymer to be crystal clear.

Other Hair Characteristics

Figure 6:
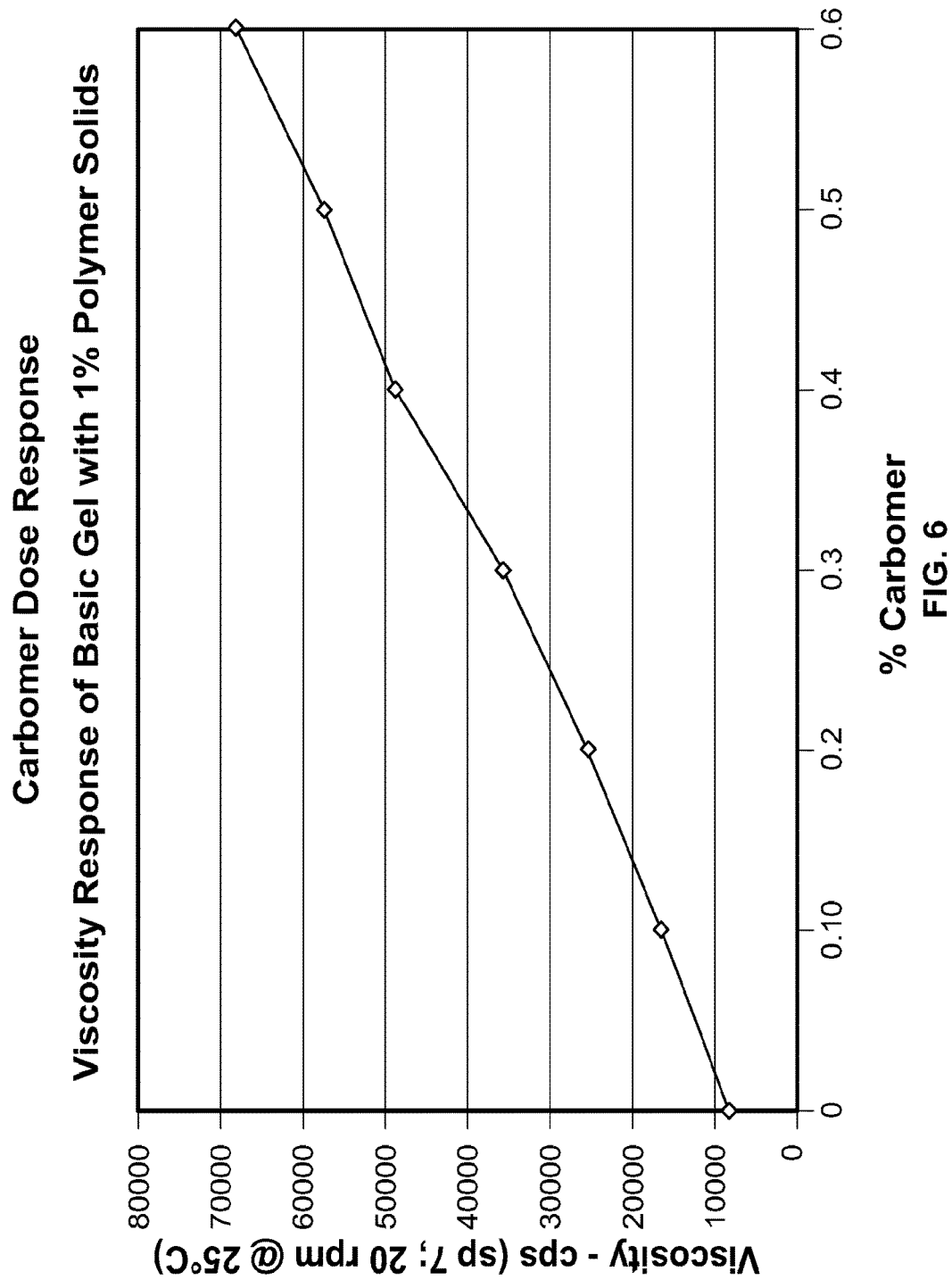
FIG. 6 is graphical presentation of viscosity response of basic gel with 1% polymer.

Other hair characteristics like shine, crunch, stiffness $5^{th}$, stiffness $10^{th}$ and curl snap are provided in FIG. 6 and compared with commercial polymers.

Viscosity Response to pH

Figure 7:
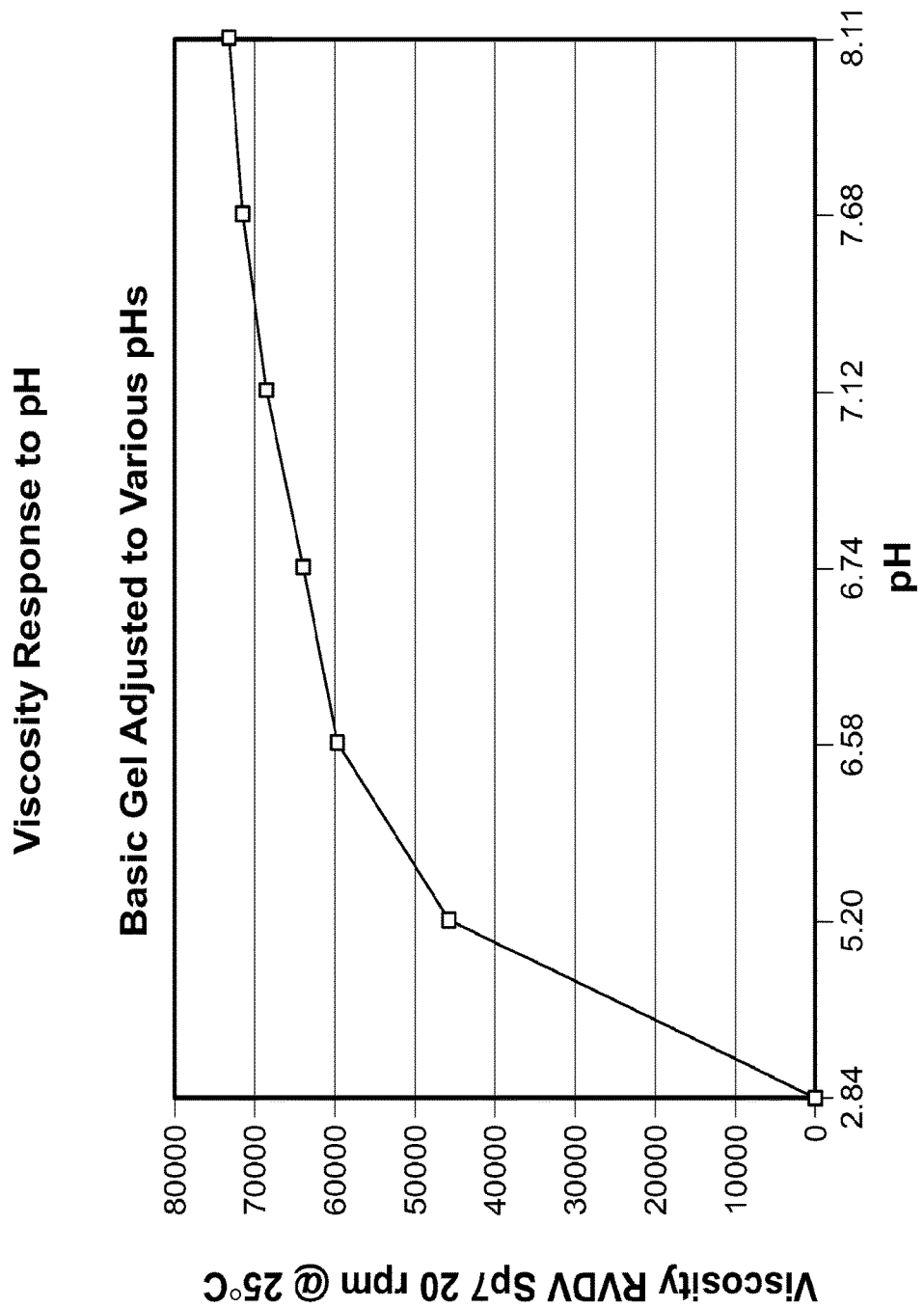
FIG. 7 is a graphical presentation of viscosity response of Inventive polymer to pH.

FIG. 7 shows an increase in viscosity of the product containing 0.6% Carbomer solids.

Figure 8:
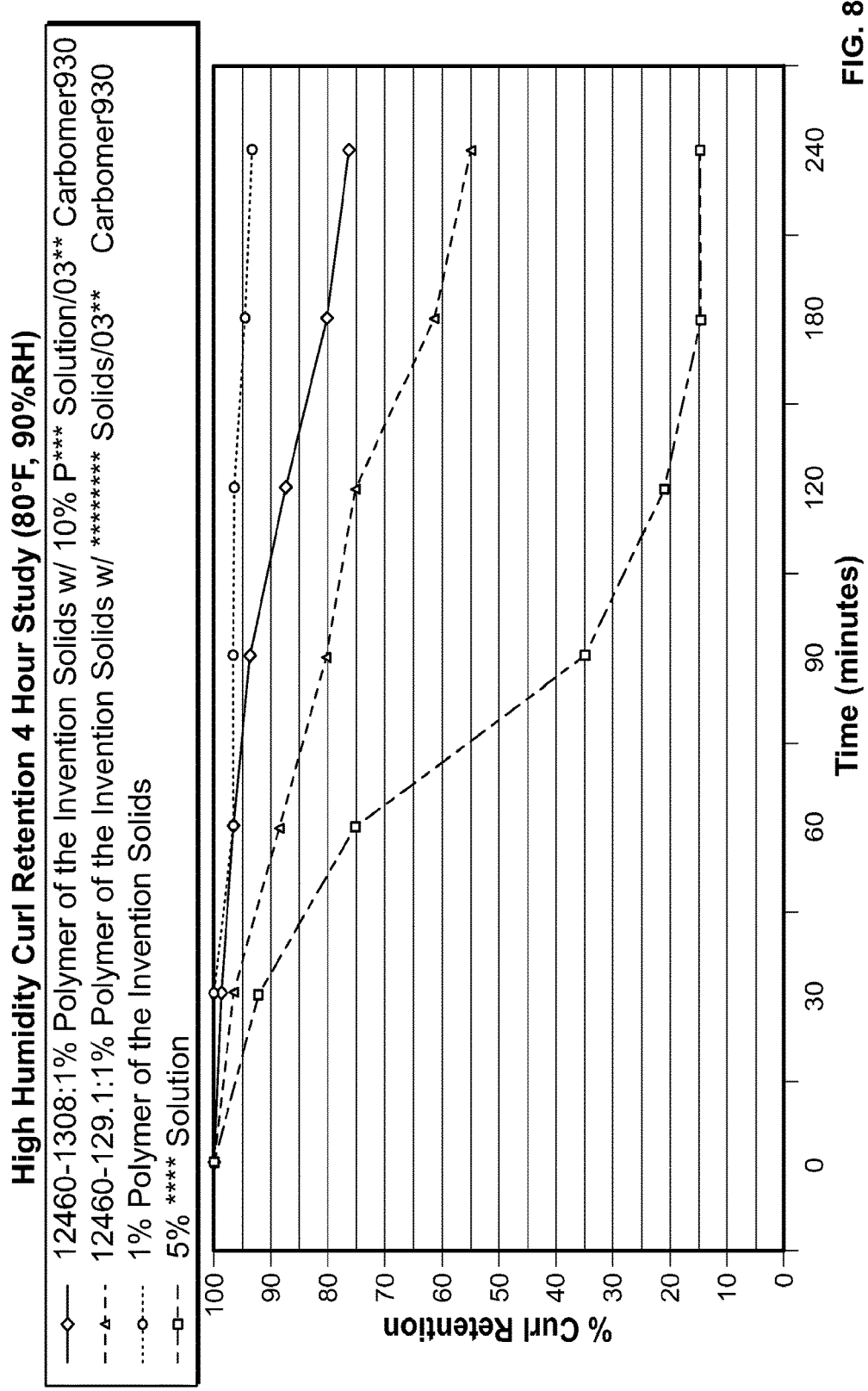
FIG. 8 is a graphical presentation of HHCR in combination with hydrophobic polymers.

FIG. 8 shows increase in viscosity of basic gel at alkaline pH (around 6.74 to 8.11)

Thus, the inventive fixative polymers have the desired properties:

Fixative polymeric gel is crystal clear showing % T more than 90;
Polymeric gel can be easily scooped from a jar;
Gel has good pick-up;
Polymeric gel spreads evenly all-through the surface;
Inventive fixative polymeric gel shows pseudo plasticity and improved rheology.
Mechanical stiffness, durability and other advanced styling benefits; and HHCR with no lag.

The following non-limiting examples illustrate specific embodiments of the present invention. They are not intended to be limiting the scope of the present invention in any way.

EXAMPLE 1

Preparation of Basic Screening Formula

Raw Materials:

| Ingredients (Trade Name | INCI/Chemical Description) | % w/w |
|---|---|---|
| Phase A | | |
| Deionized Water | Water | q.s. |
| Ashland Carbomer 980 | Carbomer | 0.6 |
| TEA 99% | TEA | q.s. pH = 7 |
| Inventive Polymer (30% Solids) | EA/MAA/PEG 25 C18 Copolymer | 3.34 |
| Liquid Germall Plus | Propylene Glycol (and) Diazolidinyl Urea (and) Iodopropynyl Butylcarbamate | 0.5 |
| | Total | 100 |

Procedure:

Water was added in a beaker and mixed with propeller at a speed enough to create a vortex. Carbomer 980 was sprinkled and mixed until the material was thoroughly dispersed.

Triethanol amine (TEA) was added to Carbomer solution and mixed until a clear thick gel was formed. Aqua Style SH-100 was added with sweep agitation and mixed until uniformity is observed. pH of the solution was adjusted to 7 using TEA. Liquid Germall Plus was added along with sufficient quantity of water.

Properties:
pH=6.8±0.2 Viscosity (Brookfield Spindle #7 @ 20 RPM @ 25C)=50,000-80,000 cps
Clarity: >90% T
Appearance: Clear, Water-white Gel

EXAMPLE 2

Effect of Low and High Level of Carbomer

| Ingredient | % Solids in ingredient | % Active in formula | Formula-1 % wt/wt | Formula-2 % wt/wt | Formula-3 % wt/wt | Formula-4 % wt/wt |
|---|---|---|---|---|---|---|
| Water | | | 93.46 | 93.46 | 93.46 | 93.46 |
| Carbomer 980 | | | 0.40 | 0.40 | 0.60 | 0.60 |
| Triethanolamine 99% | | | 1.00 | 1.00 | 1.00 | 1.00 |
| Inventive Polymer | 30% | 1.00 | 3.34 | | 3.34 | |
| Commercial Polymer | 30% | 1.00 | | 3.34 | | 3.34 |
| Liquid Germall Plus | | | 0.60 | 0.50 | 0.50 | 0.50 |
| Triethanolamine 99% | | | 0.50 | 0.50 | 0.50 | 0.50 |
| Water | | | qs | qs | qs | qs |
| Total | | | 100.00 | 100.00 | 100.00 | 100.00 | q.s.-quantity sufficient

Various samples were tested with high and low levels of Carbomer 980 and observed the physical properties thereof with comparative analysis with commercial polymers.

The results are tabulated below:

| Formula # | Polymer Type | Gel Aspect | Viscosity: Brookfield RVDV sp 7, 20 rpm @25° C. |
|---|---|---|---|
| Formula-1 | Polymer 1 | clear/smooth | 37,600 |
| Formula-2 | Commercial Polymer | clear/smooth | 9,400 |
| Formula-3 | Polymer 2 | clear/smooth | 51,400 |
| Formula-4 | Commercial Polymer | clear/smooth | 18,800 |

It was observed that the final gel was crystal clear (% T more than 90) and smooth with enhanced viscosity (more than 35,000).

EXAMPLE 3

Effect of Level of Carbomer and Fixative Polymer

| | Formula 5A | Formula 5B | Formula 5C | Formula 6A | Formula 6B | Formula 7B |
|---|---|---|---|---|---|---|
| DI Water | 93.15 | 92.25 | 94.35 | 92.5 | 90.4 | 93.26 |
| Carbomer 980 | 0.6 | 1 | 0 | 1.25 | 1.25 | 0.6 |
| TEA 99% | 2.3 | 2.8 | 1.7 | 2.4 | 2.85 | 2.3 |
| Inventive Polymer (29.8% Solids) | 3.35 | 3.35 | 3.35 | 3.35 | 5 | |
| Commercial Polymer (30% solids) | | | | | | 3.34 |
| Liquid Germall Plus | 0.6 | 0.6 | 0.6 | 0.5 | 0.5 | 0.5 |
| pH | 6.99 | 6.98 | 7.34 | 6.89 | 6.79 | 6.98 |
| Visc sp7 20 rpm | 58800 | 90800 | 9200 | 101,000 | 116,000 | 27,400 |
| %T 455 nm | 94.2 | 95 | 90.3 | 93 | 94.5 | 91.6 |
| Gel Aspect | Smooth | Smooth | Smooth | Smooth | Smooth | Smooth |

EXAMPLE 4

Spray Gel Formula

| Ingredient | Formula 8 Weight % formula |
|---|---|
| DI water | 95.62 |
| Inventive Polymer (30% solid) | 2.50 (0.75% active) |
| AMP (10% wt/wt aminoethylpropane dilution in water) | 1.88 |
| Total | 100.00 |

EXAMPLE 5

Effect on Fixative Durability Performance by Adding Hydrophilic Polymers

High humidity curl retention of hair gels with hydrophilic polymers fail especially after four hours of storage at 90% relative humidity. This can be seen in FIG. 8 for a 5% solution of PVP K-90 which is a high molecular weight version of the Polyvinylpyrrolidone (PVP). By contrast, one percent active polymer of the present invention has excellent curl retention. By combining one percent active polymer of the present invention with either a gel made with PVP K-90 or PVP K-30, a lower molecular weight version of PVP, higher levels of curl retention can be achieved by PVP. The added advantage here is that performance of conventional gels made with hydrophilic polymers can be improved by the addition of the polymer of the present invention.

EXAMPLE 6

Effect of Fixative Durability Performance with Auxiliary Fixative Polymers

Figure 9:
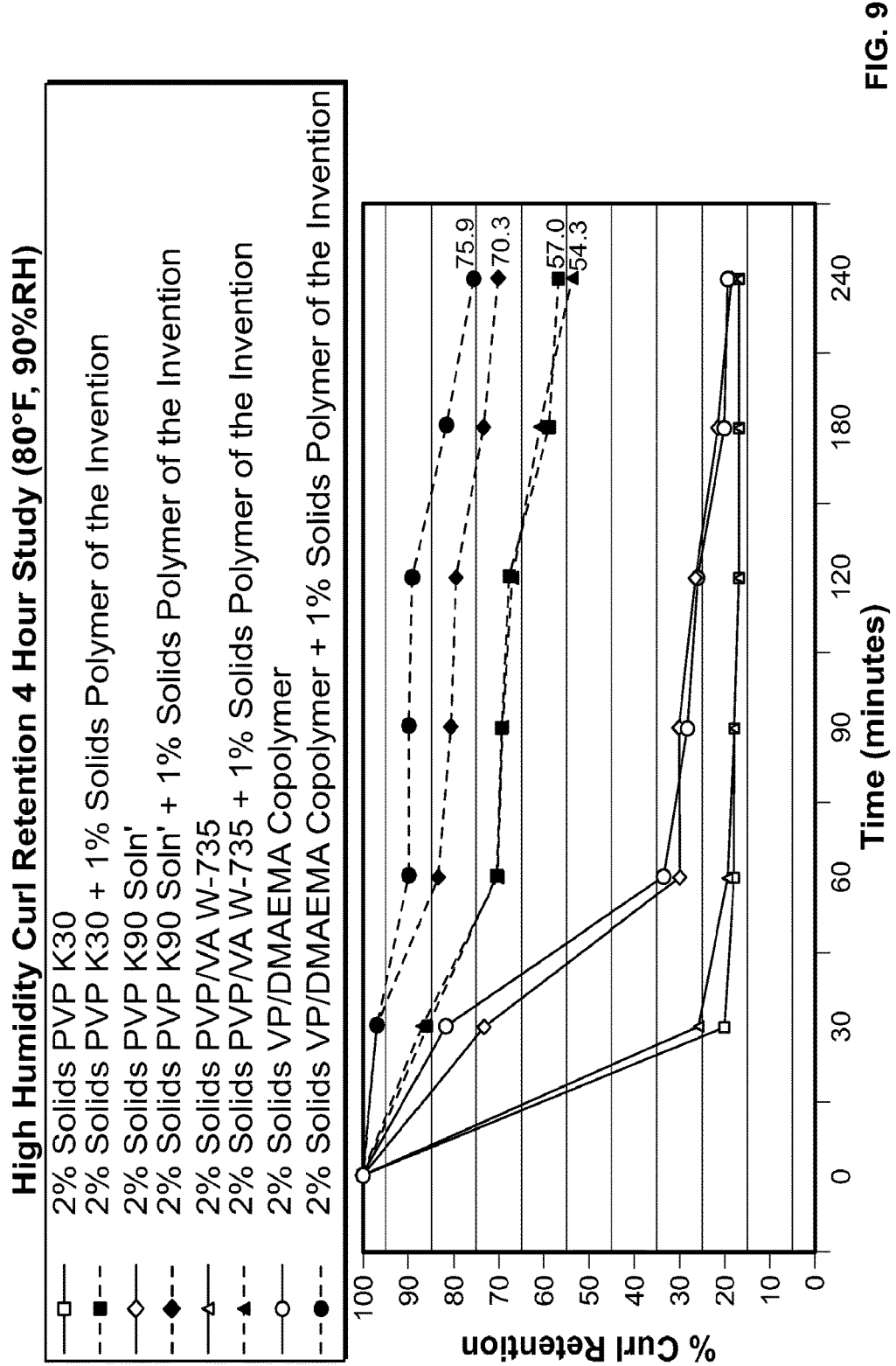
FIG. 9 is a graphical presentation of HHCR in combination with auxiliary fixing polymers.

1% solids polymer of the present invention is added in combination with a selection of various fixative polymers as listed in FIG. 9. The hydrophilic polymers, PVP K-30 and PVP K-90 have low high humidity curl retention after four hours. Copolymers of PVP, namely PVP/VA Copolymer and VP/DMAEMA Copolymer have a marginal increase in high humidity resistance over PVP based on their hydrophobic monomer compositions. Adding 1% active polymer of the present invention dramatically increases the high humidity results of all polymers as is illustrated in the chart below. As in Example 5, the added advantage is that performance of conventional gels made with not only hydrophilic polymers but also more advanced polymers for fixative performance can be improved by the addition of the polymer of the present invention.

EXAMPLE 7

Effect of Conditioning Ingredients on Fixative Durability Performance

To determine the effect of conditioning ingredients on the high humidity curl retention of the polymer of the present invention, various commonly used conditioning agents at appropriate levels were added to a basic hair gel as is illustrated below.

| Formula to determine the Impact of Conditioning Ingredients | |
| --- | --- |
| Ingredients (INCI) | % w/w |
| Phase A | |
| Water | 39.71 |
| Disodium EDTA | 0.1 |
| Carbomer | 40 |
| Polymer of the Invention | 3.34 |
| Phase B | |
| Phenoxyethanol (and) Caprylyl Glycol | 0.85 |
| Phase C | |
| Water | 10 |
| Aminomethyl Propanol | 1 |
| Phase D | |
| Conditioning Ingredient (and water) | 5 |
| Total | 100 |

Figure 10:
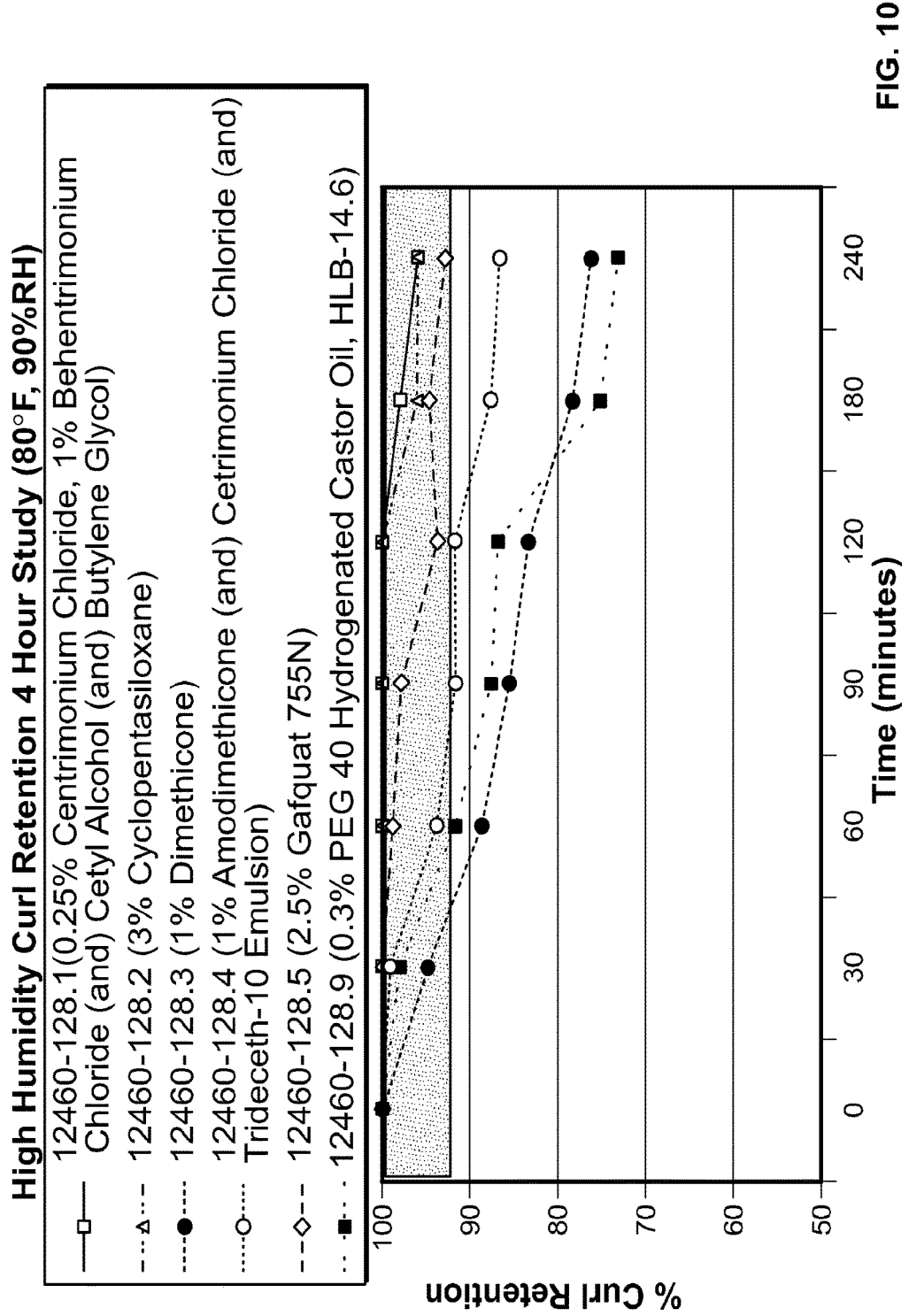
FIG. 10 is a graphical presentation of HHCR with conditioning ingredients.

In general conditioning agents used to soften and smooth the hair tend to reduce the fixative durability of the styling polymer especially with respect to high humidity curl retention. However, as can be seen in FIG. 10, only minor decreases in humidity resistance are observed. This suggests that not only can the fixative performance of hydrophilic polymers being increased by the addition of the polymer of the present invention, but also the polymer of the present invention is not affected by those ingredient that tend to lower fixative efficacy such as conditioning agents.

EXAMPLE 8

Thickener Free Clear Hair Gel

To demonstrate the two in one functionality of the polymer of the present invention, a hair gel was made without a conventional thickening agent such as carbomer. The formula below contains 2% active of the polymer of the present invention with PVP as an auxiliary polymer. A viscosity of 24,000 cps was achieved by measuring the gel with an RV type Brookfield viscometer using spindle 7 rotating at 10 rpm. pH of the gel was 6.97 and was crystal clear with an NTU reading of 3.16 taken with a turbidometer. This example shows that a thickening polymer is not necessary to produce thick efficacious hair gels using the polymer of the present invention.

| 24 h Thickener Free Clear Gel | |
| --- | --- |
| Ingredients (INCI) | % w/w |
| Phase A | |
| Water | 68.38 |
| Disodium EDTA | 0.10 |
| Polymer of the invention | 6.67 |
| PEG/PPG-25/25 DIMETHICONE | 0.35 |
| Phase B | |
| Phenoxyethanol (and) Caprylyl Glycol | 0.85 |
| Phase C | |
| Water | 10.00 |
| Glycerin | 3.00 |
| Aminomethyl Propanol | 0.65 |
| Phase D | |
| Polyvinylpyrrolidone | 10.00 |
| | 100.00 |

EXAMPLE 9

Formula with Combination of Conditioning Agents

Figure 11:
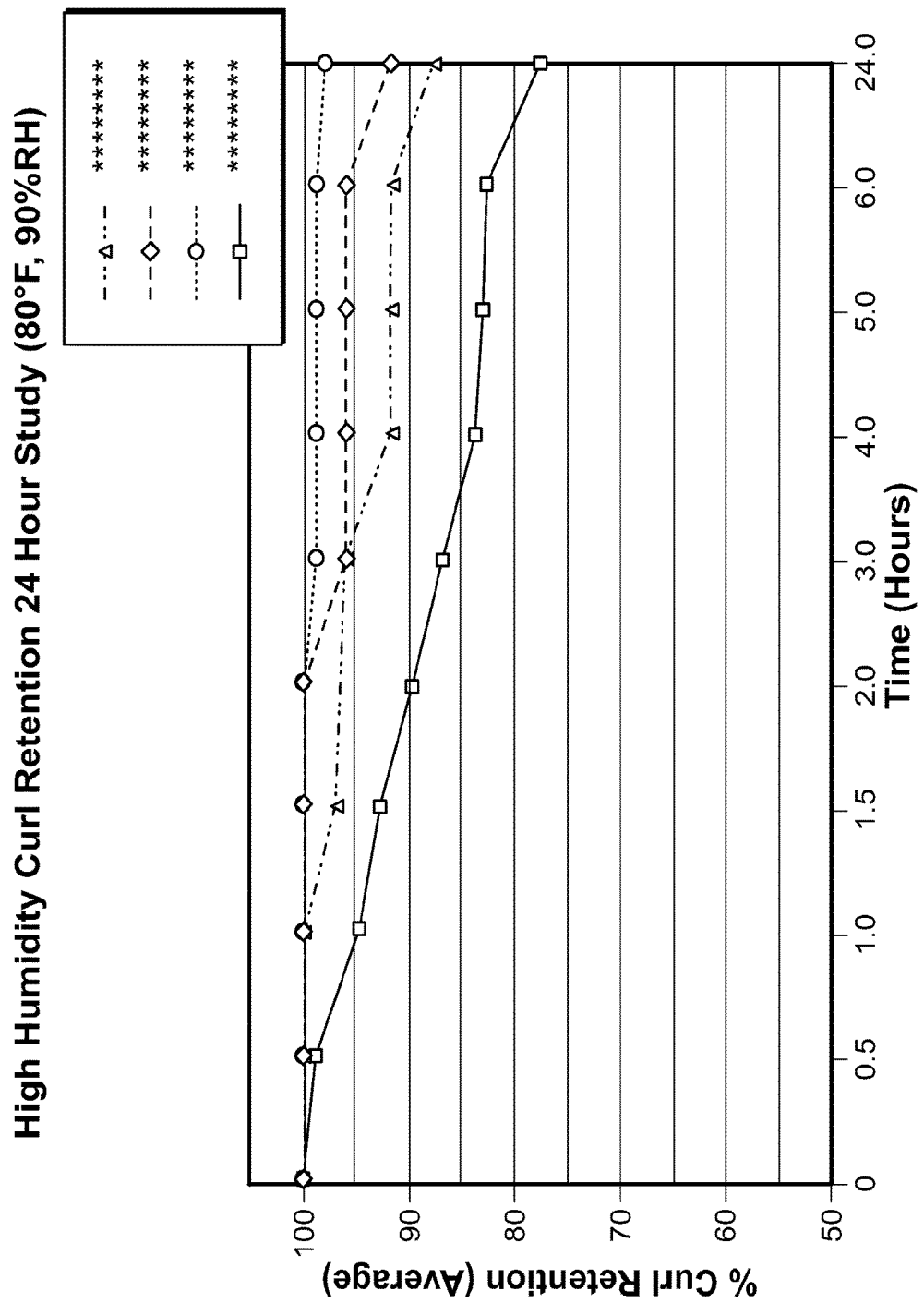
FIG. 11 is a graphical presentation of HHCR with combinations of conditioning ingredients.

Example 9 illustrated the minimal effect on lowering high humidity curl retention when a particular conditioning agent is used in combination with the polymer of the present invention. FIG. 11 shows a formula where there is a combination of different classes of conditioning ingredients. These include a conditioning polymer, Polyquaternium-11, cationic surfactants, emollient esters, and silicone oils. The high humidity chart below shows a minimal decrease in fixative polymer durability despite the high number of conditioning ingredients incorporated into the formula.

| Lasting Style and Moisturizing Cream | |
| --- | --- |
| Ingredients (INCI) | % w/w |
| Phase A | |
| Deionized Water | 78.63 |
| Butylene Glycol | 2 |

-continued

Lasting Style and Moisturizing Cream

| Ingredients (INCI) | % w/w |
|---|---|
| 1,2-Hexanediol | 1 |
| Polymer of the Invention | 6.67 |
| Aminomethyl Propanol | 0.4 |
| Phase B | |
| | |
| Glyceryl Stearate (and) PEG-100 Stearate | 0.25 |
| Behentrimonium methosulfate (and) C10-40 isoalkylamidopropylethyldimonium ethosulfate (and) cetyl alcohol | 0.8 |
| Quaternium-91 (and) Cetrimonium Methosulfate (and) Cetearyl Alcohol | 0.4 |
| Isodecyl Neopentanoate | 0.7 |
| Octyldodecyl Stearoyl Stearate | 1 |
| Phase C | |
| | |
| Cyclomethicone | 3 |
| Dimethicone | 1 |
| Ethylhexyl Methoxycinnamate | 0.25 |
| Phenoxyethanol (and) Caprylyl Glycol | 1.25 |
| D&C Violet #2 | 0.0002 |
| Phase D | |
| | |
| Polyquaternium-11 | 2.5 |
| Aminomethyl Propanol | 0.15 |
| | 100 |

EXAMPLE 10

Figure 12:
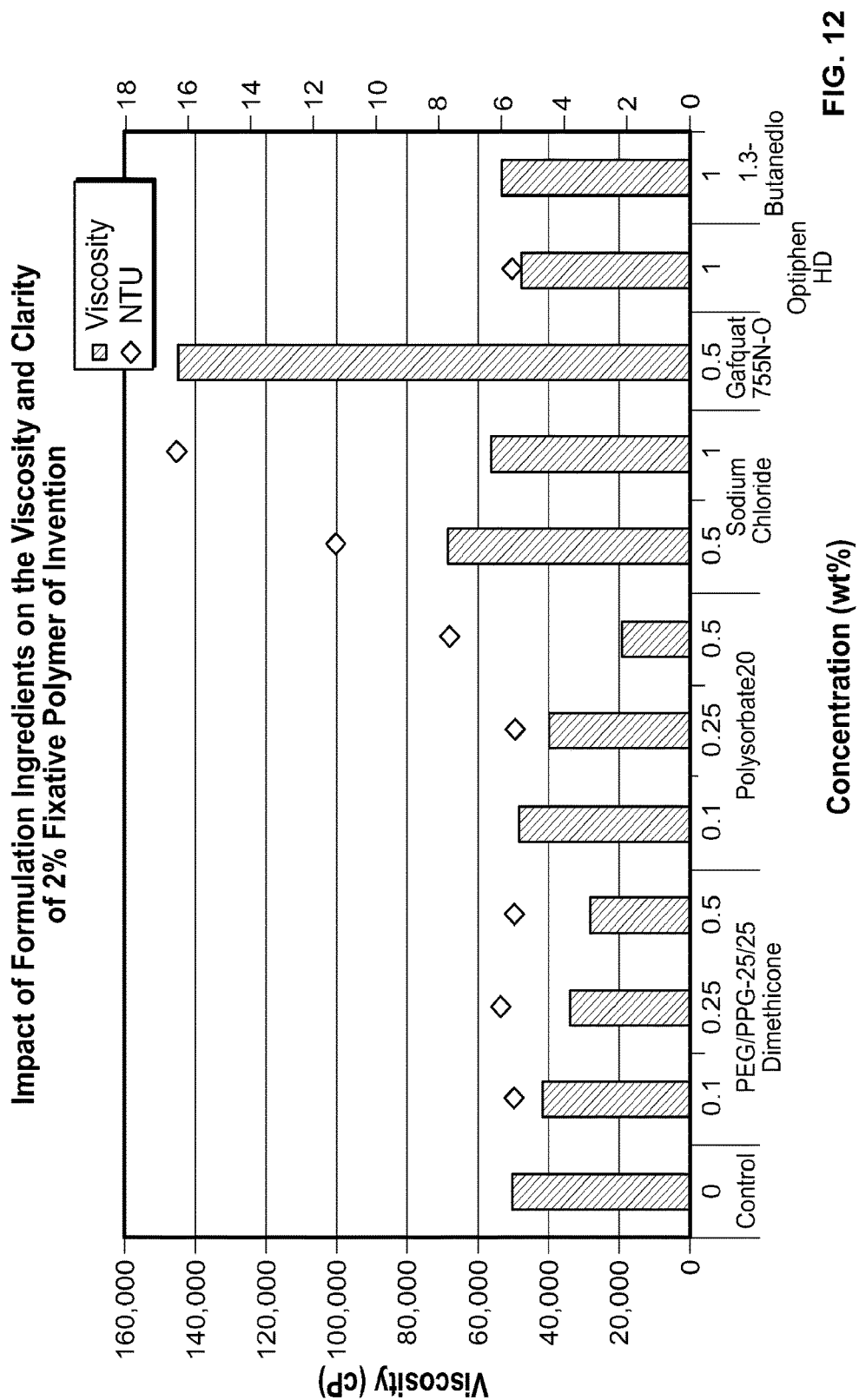
FIG. 12 is a graphical presentation of the impact of additional formulation ingredients on viscosity and clarity.

Effect of Common Auxiliary Ingredients Found in Styling Products on Performance Properties of Polymer of the Invention FIG. 12 indicates the effect of various commonly used ingredients on the viscosity and transparency of 2% active polymer of the invention. The following observations can be made:

1. PEG/PPG-25/25 Dimethicone, a common water soluble conditioning agent, has a slight negative effect on viscosity and little effect on clarity.
2. Polysorbate 20 a nonionic surfactant and common fragrance solubilizer lowers the viscosity of the gel especially at 0.5% but is still acceptable. Little effect is noted on clarity.
3. Adding salt has a negative effect on clarity which is common for acrylate based thickeners.
4. A synergistic effect on viscosity is noted when Polyquaternium-11 (Gafquat 755N made by Ashland, Inc.) is added to the polymer of this invention. This is due to the association of the cationic quaternary group of Polyquaternium-11 and the anionic (meth) acrylic acid groups of the polymer of the invention. Although this combination is hazy, the synergy in viscosity could have a positive effect in some formulation such as cream gels where clarity is not a concern.

Figure 13:
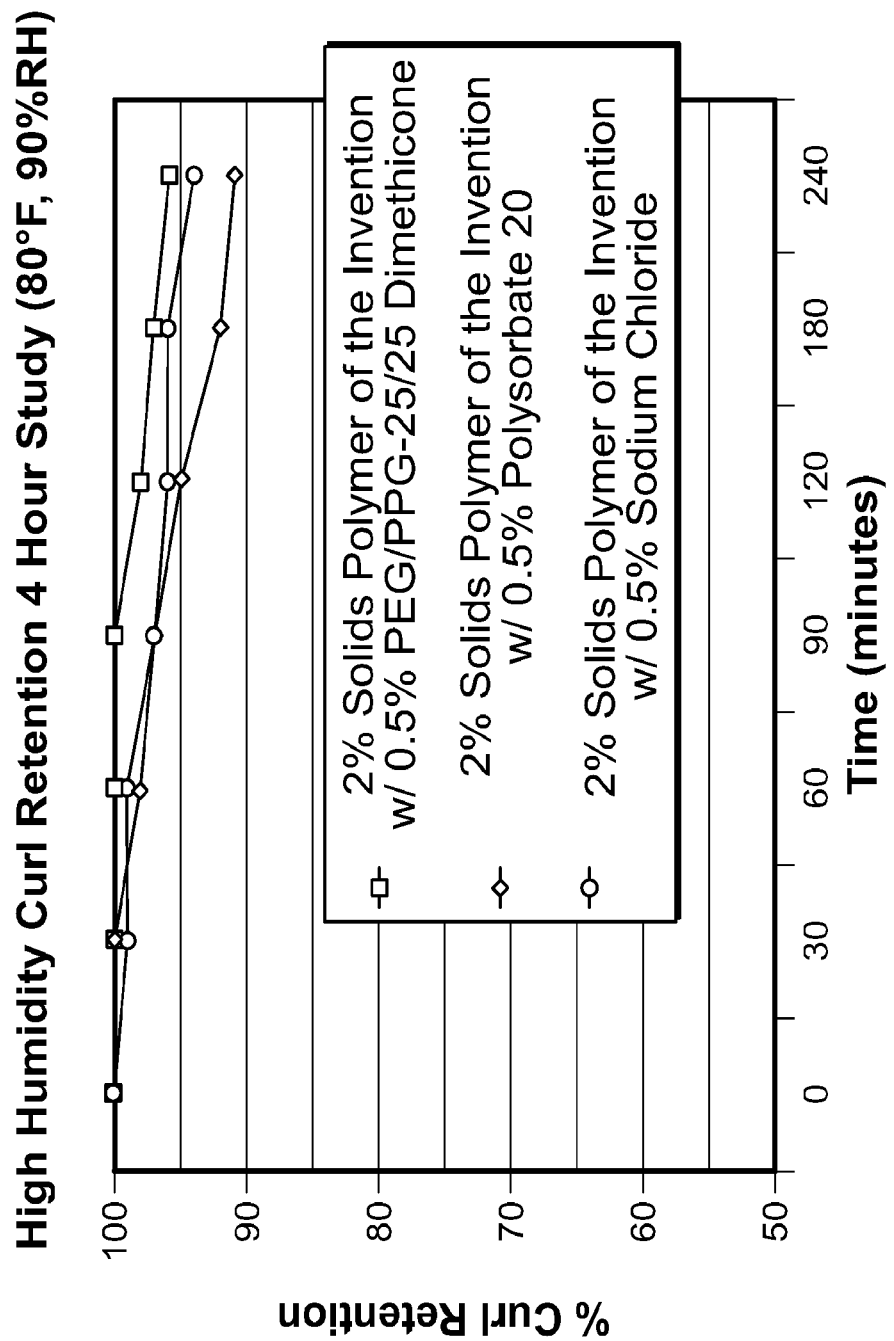
FIG. 13 is a graphical presentation of the impact of additional formulation ingredients on HHCR.

In FIG. 13, a select number of additives were combined with the polymer of the invention and tested for fixative durability at high humidity. Results indicate little negative effect.

The invention has been described in detail with particular reference to preferred embodiments thereof, but it will be understood that variations and modifications can be effected within the spirit and scope of the invention.

We claim:

1. A personal care composition comprising:
   a) a fixative polymer consisting of:
      55-60% by weight of ethyl acrylate;
      30-50% by weight of (meth) acrylic acid;
      1-5% by weight of an associative monomer comprising a methacrylic ester with an oxyalkylated ethylenic unsaturation terminated by a hydrophobic, non-aromatic branched chain with 12to 22 carbon atoms;
      0. 1-4% by weight of a cross-linking agent;
   b) one or more of personal care additives; and
   c) an aqueous carrier;
   Wherein the personal care composition is a clear gel having clarity of at least 90% as measured by T (transmittance).

2. The composition of claim 1, wherein said personal care additives are selected from auxiliary fixing agents, surfactant, initiators, preservatives, neutralizing agents, emulsion stabilizers, anti-static agents, cosmetic agents or combinations thereof.

3. The composition of claim 2, wherein said surfactant is selected from sodium lauryl sulfate, sodium laureth sulfate, ammonium laureth sulfate and sodium cocoyl isethionate; cationic surfactants selected from cetyltrimethyl ammonium chloride, lauryl dimethyl benzyl ammonium chloride or amphoteric surfactants selected from polyoxyethyleneated alkylphenols, polyoxyethyleneated straight chain alcohols, polyoxyethyleneated branched chain alcohol and combinations thereof.

4. The composition of claim 1, wherein said fixative polymer when neutralized to alkaline pH has improved rheology and viscosity.

5. The composition of claim 1, wherein said composition used in hair styling has at-least 90% high humidity curl retention.

6. The composition of claim 1, wherein said composition has stiffness durability of at-least 0.7.

7. The composition of claim 2, wherein said auxiliary fixing agent is selected from the group consisting of PVP, VP/VA Copolymer, VP/DMAEMA Copolymer, Polyquaternium-69, and Octylacrylamide/Acrylates/Butylaminoethyl Methacrylate Copolymer.

* * * * *